United States Patent [19]

Winter et al.

[11] Patent Number: 5,095,062

[45] Date of Patent: Mar. 10, 1992

[54] STABILIZED COMPOSITIONS CONTAINING LIQUID SUBSTITUTED 2H-BENZOTRIAZOLE MIXTURES

[75] Inventors: Roland A. E. Winter, Armonk; Robert E. Detiefsen, Putnam Valley, both of N.Y.; Werner Stegmann, Liestal, Switzerland; Reto Luisoli, Holstein, Switzerland; David Leppard, Marly, Switzerland

[73] Assignee: Ciba-Geigy Corporation, Ardsley, N.Y.

[21] Appl. No.: 578,059

[22] Filed: Sep. 5, 1990

Related U.S. Application Data

[62] Division of Ser. No. 179,737, Apr. 11, 1988, Pat. No. 4,973,701.

[51] Int. Cl.$^5$ ............................................. C08K 5/3472
[52] U.S. Cl. ...................................... 524/91; 548/260; 252/401
[58] Field of Search ........................... 524/91; 548/260; 252/401

[56] References Cited

U.S. PATENT DOCUMENTS

| | | | |
|---|---|---|---|
| 3,004,896 | 10/1961 | Heller et al. | 424/59 |
| 3,055,896 | 9/1962 | Boyle et al. | 548/260 |
| 3,072,585 | 1/1963 | Milionis et al. | 528/396 |
| 3,074,910 | 1/1963 | Dickson | 524/91 |
| 3,189,615 | 6/1965 | Heller et al. | 524/91 |
| 3,230,194 | 1/1966 | Boyle | 524/91 |
| 3,253,921 | 5/1966 | Sawdey | 430/17 |
| 3,983,132 | 9/1976 | Strobel | 524/91 |
| 4,042,394 | 8/1977 | Smith, Jr. et al. | 430/17 |
| 4,096,242 | 6/1978 | Strobel | 429/59 |
| 4,127,586 | 11/1978 | Rody et al. | 524/91 |
| 4,129,521 | 12/1978 | Strobel | 524/91 |
| 4,278,590 | 7/1981 | Dexter et al. | 524/91 |
| 4,283,327 | 8/1981 | Dexter et al. | 524/91 |
| 4,383,863 | 5/1983 | Dexter et al. | 106/125 |
| 4,447,511 | 5/1984 | Dexter et al. | 430/15 |
| 4,587,346 | 5/1986 | Winter et al. | 548/260 |
| 4,675,352 | 6/1987 | Winter et al. | 524/91 |
| 4,973,701 | 11/1990 | Winter et al. | 548/260 |

*Primary Examiner*—Kriellion S. Morgan
*Assistant Examiner*—Tae H. Yoon
*Attorney, Agent, or Firm*—Luther A. R. Hall

[57] ABSTRACT

Liquid substituted, 2H-benzotriazole mixtures are prepared by alkylation with concomitant dealkylation, fragmentation and realkylation of 2-(2-hydroxy-5-alkylphenyl)-2H-benzotriazoles or of 2-(2-hydroxy-3,5-dialkylphenyl)-2H-benzotriazoles with straight or branched alkenes of 8 to 30 carbon atoms in the presence of an acid catalyst at 100°-200° C. The liquid mixtures exhibit outstanding efficacy in protecting organic substrates from light induced deterioration as well as good resistance to loss by volatilization or exudation during the processing of stabilized compositions at elevated temperatures.

7 Claims, No Drawings

STABILIZED COMPOSITIONS CONTAINING LIQUID SUBSTITUTED 2H-BENZOTRIAZOLE MIXTURES

This is a divisional of application Ser. No. 179,737, filed on Apr. 11, 1988, now U.S. Pat. No. 4,973,701, issued on Nov. 27, 1990.

BACKGROUND OF THE INVENTION

The present invention relates to selected liquid 2-aryl-2H-benzotriazoles which are useful in protecting light-sensitive organic materials from deterioration and to stabilized compositions containing said benzotriazoles.

The UV-absorber of the o-hydroxyphenyl-2H-benzotriazole class have long been known as effective light stabilizers for organic materials and have enjoyed considerable commercial success.

The description, preparation and uses of these valuable 2-aryl-2H-benzotriazoles are further taught in U.S. Pat. Nos. 3,004,896; 3,055,896; 3,072,585; 3,074,910; 3,189,615 and 3,230,194.

However the hitherto known 2-aryl-2H-benzotriazoles of this group have in some circumstances exhibited limited compatibility in certain substrates, and excessive tendency to exude, sublime and/or volatilize during processing of stabilized compositions into sheets, films, fibers or other pellicles when processing must be done at elevated temperatures. Likewise such benzotriazoles may also suffer undue loss by volatilization or sublimation from fabricated structures, particularly thin films or coatings, especially when subjected to elevated temperatures during use.

Attempts have been made to increase compatibility and to reduce volatilization loss by modifying the structure of the benzotriazoles.

In U.S. Pat. No. 3,230,194, a higher alkyl group was substituted for methyl and the latter compound 2-(2-hydroxy-5-tert-octylphenyl)-2H-benzotriazole exhibited superior compatibility and performance in polyethylene compared to the former.

In U.S. Pat. Nos. 4,283,327, 4,278,590 and 4,383,863 there is described 2-(2-hydroxy-3,5-di-tert-octylphenyl)-2H-benzotriazole which exhibits an excellent combination of compatibility with and/or solubility in numerous polymeric substrates along with superior resistance to loss from stabilized compositions during high temperature processing or in end-use applications where coatings or films of the stabilized compositions are exposed even to ambient weathering and light exposures, and in photographic applications. However, 2-(2-hydroxy-3,5-di-tert-octylphenyl)-2H-benzotriazole is still a solid (melting point 105°-106° C.) which requires in many end-use applications the concomitant use of a solvent or dispersing diluent to allow for it to be used in practice. Such solvents or diluents are undesired for reasons of cost and environmental and other considerations.

U.S. Pat. Nos. 3,983,132, 4,096,242 and 4,129,521 describe liquid mixtures of 2-(2-hydroxy-5-nonylphenyl)-2H-benzotriazoles or of 2-(2-hydroxy-5-dodecylphenyl)-2H-benzotriazoles and stabilized compositions using said mixtures where the nonyl or dodecyl groups each represent an isomeric mixture of secondary and tertiary nonyl or dodecyl groups attached to the para position relevant to the hydroxy group on the 2-phenyl moiety in the 2H-benzotriazole. The isomeric nonyl or dodecyl groups are introduced into the phenol before it is coupled with the 2-nitrophenyldiazonium salt in a classic 2H-benzotriazole synthesis.

The instant liquid benzotriazoles differ from the benzotriazoles of these three patents by the method by which they are prepared, by the location of the branched alkyl group ortho to the hydroxy group and by in part the nature of the branched alkyl group itself when prepared from a straight chain alkene.

The liquid mixtures prepared by the method of U.S. Pat. No. 4,129,521 have no substitution in the ortho position relevant to the hydroxy group thus making said compounds prone to interaction with metal ions during resin curing and in other end-use applications in polymer substrates and which may lead to deleterious effects on color, light stability and ancillary properties. The instant mixtures are substituted in the ortho position relevant to the hydroxyl group and do not have this problem.

Certain hydrophobic non-diffusing hydroxyphenyl-benzotriazoles are disclosed as very useful as ultraviolet light absorbers in photographic gelatin layers (U.S. Pat. No. 3,253,921). The instant benzotriazoles with their liquid or non-crystalline nature, their desirable absorption characteristics in the ultraviolet range and their photographic inertness are particularly useful in photographic compositions, especially in protecting color dye images against the harmful effects of ultraviolet light.

U.S. Pat. No. 3,253,921 discloses benzotriazoles broadly, but does not exemplify the instant benzotriazoles which are particularly effective in stabilizing photographic compositions against the harmful effects of ultraviolet radiation.

Further background in the area of stabilization of photographic dye images is provided by U.S. Pat. No. 4,042,394 which describes the various components in photographic compositions and the requirements for stabilizing photographic dye images.

U.S. Pat. Nos. 4,383,863 and 4,447,511 describe the use of 2-(2-hydroxy-3,5-di-tert-octylphenyl)-2H-benzotriazole in photographic elements and compositions. While this discrete benzotriazole exhibits enhanced solubility in the various solvents and diluents used in photographic elements, such solvents and diluents are still required since said benzotriazole is still a crystalline solid.

The instant benzotriazole mixtures are liquid or non-crystalline leading to the need for less or no solvent or diluent, thinner photographic layers and all the concomitant economic benefits flowing therefrom.

U.S. Pat. No. 4,127,586 teaches that it is possible to alkylate phenols with long chain olefins to get a phenol substituted with a mixture of isomers as the alkyl substituents. The corresponding 2H-benzotriazole is then prepared by the classic diazotizing, coupling and reduction route starting with o-nitroaniline. The 2H-benzotriazole prepared by this classic method differs in the distribution of isomeric components and in chemical properties from the instant products made by an entirely different process.

U.S. Pat. Nos. 4,587,346 and 4,675,352 pertain to the alkylation of preformed 2-(2-hydroxy-5-methylphenyl)-2H-benzotriazole using a long straight or branched alkene in the presence of an acid catalyst at 100°-200° C. Liquid mixtures are obtained by this process, but the final products always contain a 5-methyl substituent. The instant process and products differ from those of these two patents. The 5-methyl group is unaffected by the process conditions used neither being displaced, rearranged or disproportionated during the alkylation process of said patents.

The instant process and products differ markedly from this situation since the higher alkyl groups on the 3 and/or 5-positions can be displaced, rearranged, dealkylated or fragmented during the instant process giving a quite different melange of useful products from the preformed starting 2H-benzotriazoles and the liquid products of the prior art.

DETAILED DISCLOSURE

This invention pertains to selected liquid or non-crystalline 2-aryl-2H-benzotriazole light absorbers and to organic materials, both polymeric and non-polymeric, stabilized thereby, as well as to photographic elements containing said liquid materials. The stabilized compositions include plastics, coatings, fibers, films, and photographic substrates.

Another object of this invention is the process for preparing said liquid or non-crystalline mixtures of benzotriazoles. These liquid mixtures exhibit great resistance to volatilization, enhanced solubility in selected solvents, desirable absorption characteristics in the ultraviolet range and photographic inertness. This combination of properties makes these benzotriazoles particularly useful in photographic compositions especially in protecting color dye images against the harmful effects of ultraviolet light.

More particularly, the instant invention pertains to a normally liquid or non-crystalline mixture of benzotriazoles, suitable for stabilizing organic materials against light-induced deterioration, which consists essentially of compounds of the formula

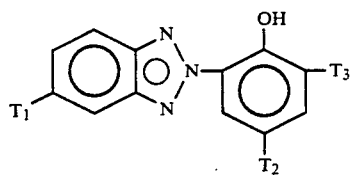

(I)

wherein $T_1$ is hydrogen, chloro, alkyl of 1 to 4 carbon atoms or alkoxy of 1 to 4 carbon atoms, and where one of $T_2$ or $T_3$ is a random of at least three isomeric alkyl groups each having 8 to 40 carbon atoms, and the other of $T_2$ or $T_3$ is hydrogen or methyl, and where one of $T_2$ or $T_3$ is a random statistical mixture as defined above and the other of $T_2$ or $T_3$ is alkyl of 2 to 12 carbon atoms, cycloalkyl of 5 to 8 carbon atoms or aralkyl of 7 to 9 carbon atoms; and in minor proportions compounds where both of $T_2$ and $T_3$ are a random statistical mixture as defined above or where the compounds represent dealkylated or fragmented-alkyl substituted products of the benzotriazoles of formula I which mixture is prepared by reacting a 2H-benzotriazole of formula (A) or (B)

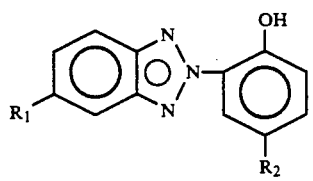

(A)

or

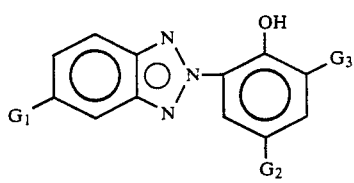

(B)

where $R_1$ is hydrogen, chloro, alkyl of 1 to 4 carbon atoms or alkoxy of 1 to 4 carbon atoms, $R_2$ is alkyl of 2 to 12 carbon atoms, cycloalkyl of 5 to 8 carbon atoms or aralkyl of 7 to 9 carbon atoms, $G_1$ has the same meaning as $R_1$, and $G_2$ and $G_3$ are independently branched alkyl of 3 to 12 carbon atoms, cycloalkyl of 5 to 8 carbon atoms or aralkyl of 7 to 9 carbon atoms, or one of $G_2$ and $G_3$ is methyl or ethyl when the other of $G_2$ and $G_3$ is branched alkyl, cycloalkyl or aralkyl as defined above, with a straight or branched chain alkene of 8 to 40 carbon atoms or mixture of said alkenes in the presence of an acidic catalyst at a temperature of 100° to 200° C.

Preferably $T_1$, $R_1$ and $G_1$ are hydrogen or chloro; most preferably hydrogen.

Preferably $T_2$ or $T_3$ in the random statistical mixture of alkyl groups is alkyl of 8 to 16 carbon atoms; most preferably alkyl of 10 to 12 carbon atoms.

Preferably when $T_2$ or $T_3$ is not the random statistical mixture of alkyl groups, $T_2$ or $T_3$ is hydrogen, branched alkyl of 4 to 8 carbon atoms or alpha,alpha-dimethylbenzyl, but $T_2$ and $T_3$ are not both hydrogen at the same time.

Preferably $R_2$ or $G_2$ and $G_3$ are independently branched alkyl of 3 to 12 carbon atoms or aralkyl of 7 to 9 carbon atoms, or $R_2$ or one of $G_2$ or $G_3$ is methyl or ethyl and the other of $G_2$ or $G_3$ is branched alkyl of 3 to 12 carbon atoms.

When $R_2$, $G_2$ or $G_3$ is branched alkyl of 3 to 12 carbon atoms, said alkyl is for example isopropyl, sec-butyl, tert-butyl, tert-amyl, tert-octyl or tert-dodecyl. When $R_2$, $G_2$ or $G_3$ is aralkyl of 7 to 9 carbon atoms, said aralkyl is benzyl, alpha-methylbenzyl or alpha,alpha-dimethylbenzyl.

The 2-(2-hydroxyphenyl)-2H-benzotriazole light absorbers are conventionally obtained by coupling an appropriately substituted phenol with an o-nitrophenyl diazonium salt to prepare an o-nitroazobenzene intermediate which is subsequently reduced and cyclized to the corresponding 2H-benzotriazole.

It is clear that any change in the nature of the substitution on the phenol moiety, for example for the purpose of modifying final 2H-benzotriazole properties, must be carried out on the phenol molecule itself before the conventional 2H-benzotriazole synthesis is begun. This requires one or more additional steps in the synthetic sequence for each new 2H-benzotriazole product. Moreover, unavoidable side reactions occur during these steps which make it necessary to include at least one crystallization step in order to obtain a product of acceptable purity.

The above procedure is poorly adapted for the preparation of non-crystalline or liquid products where purification by crystallization is not possible.

Indeed the process described in U.S. Pat. No. 4,129,521 discloses that, in order to obtain liquid products of acceptable purity, it is necessary to (1) vacuum distill the crude 2H-benzotriazole product, treat the once distilled product with acetic anhydride to remove various undesirable impurities; carry out a second vacuum distillation on the acetylated mixture; blow the distillate with air at elevated temperature for many hours and finally distill the material for a third time under molecular distillation conditions. Only then after these laborious and economically unattractive procedures is a liquid product useful as a light absorber obtained.

Clearly a better method of making liquid or non-crystalline 2H-benzotriazoles was needed since the conventional approach of preparing an alkylated phenol and then the benzotriazole from said phenol involves an almost impossible task of removing undesirable impurities from the benzotriazole in a practical manner.

The approach of alkylating a preformed 2H-benzotriazole was not believed promising since it was known that phenols substituted in the ortho position by a 2H-benzotriazolyl moiety are vastly deactivated in respect to electrophilic substitution (= alkylation) on the phenolic ring.

It was thus surprising that direct alkylation on the phenolic ring of preformed 2H-benzotriazoles could be carried out to give the desired mixed alkylated products in a facile and direct manner.

As described in U.S. Pat. Nos. 4,587,346 and 4,675,352, the direct alkylation of 2-(2-hydroxy-5-methylphenyl)-2H-benzotriazole with an alpha-olefin or straight chain alkene; or with a branched alkene occurred in excellent conversions (over 90%) of the preformed benzotriazole to alkylated products.

Since the 2-(2-hydroxy-5-methylphenyl)-2H-benzotriazole is already substituted in the para position to the hydroxyl group, alkylation is perforce directed to the ortho position to the hydroxyl moiety to obtain a mixture of 2-(2-hydroxy-3-higher branched alkyl-5-methylphenyl)-2H-benzotriazoles.

The nature of the random statistical mixture of alkyl groups that are inserted into the 2H-benzotriazoles of formula I as $T_2$ or $T_3$ depends on which type of alkene is used for the alkylation.

The use of an alpha-olefin or straight chain alkene leads to the insertion of branched secondary alkyl groups while the use of a branched alkene leads to branched alkyl groups having a multiplicity of alkyl branches along the main alkyl chain.

The 2H-benzotriazoles used as starting materials in the instant invention differ significantly from the 2-(2-hydroxy-5-methylphenyl)-2H-benzotriazole used in the prior art process.

Whereas the methyl group in the 5-position of 2-(2-hydroxy-5 methylphenyl)-2H-benzotriazole is not labile, is not displacable and cannot be fragmented, alkylation in the prior art process is perforce directed solely to the unsubstituted ortho position to the hydroxyl moiety.

This is not the case with the instant 2H-benzotriazole which fall into two categories (A) and (B):

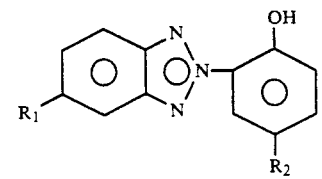

(A)

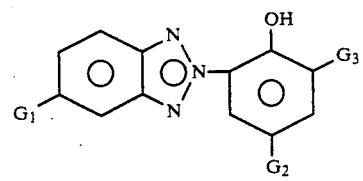

(B)

wherein
$R_1$ is hydrogen, chloro, alkyl of 1 to 4 carbon atoms or alkoxy of 1 to 4 carbon atoms,
$R_2$ is alkyl of 2 to 12 carbon atoms, cycloalkyl of to 8 carbon atoms or aralkyl of 7 to 9 carbon atoms,
$G_1$ has the same meaning as $R_1$, and
$G_2$ and $G_3$ are independently a branched alkyl of 3 to 12 carbon atoms, cycloalkyl of 5 to 8 carbon atoms or aralkyl of 7 to 9 carbon atoms, or one of $G_2$ and $G_3$ is methyl or ethyl when the other of $G_2$ or $G_3$ is branched alkyl, cycloalkyl or aralkyl as defined above.

More particularly, the instant process is a process for preparing a normally liquid or non-crystalline mixture of benzotriazoles, suitable for stabilizing organic materials against light induced deterioration, which consists essentially of the formula

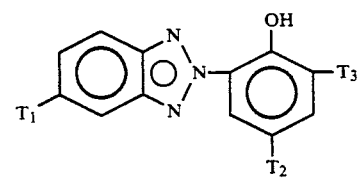

(I)

wherein
$T_1$ is hydrogen, chloro, alkyl of 1 to 4 carbon atoms or alkoxy of 1 to 4 carbon atoms, and
in major proportions compounds
where one of $T_2$ or $T_3$ is a random statistical mixture of at least three isomeric alkyl groups each having 8 to 40 carbon atoms, and
the other of $T_2$ or $T_3$ is hydrogen or methyl, and
where one of $T_2$ or $T_3$ is a random statistical mixture as defined above and the other of $T_2$ or $T_3$ is alkyl of 2 to 12 carbon atoms, cycloalkyl of 5 to 8 carbon atoms or aralkyl of 7 to 9 carbon atoms; and
in minor proportions compounds where both of $T_2$ and $T_3$ are a random statistical mixture as defined above or where the compounds represent dealkylated or fragmented-alkyl substituted products of the benzotriazoles of formula I
which process comprises
reacting a 2H-benzotriazole of the formula (A) or (B)

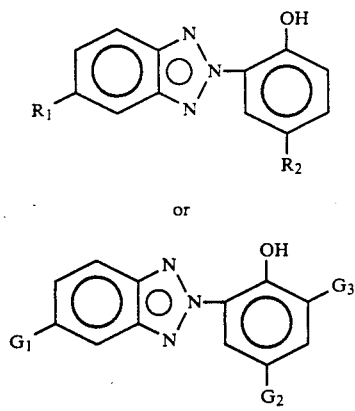

wherein

R₁ is hydrogen, chloro, alkyl of 1 to 4 carbon atoms or alkoxy of 1 to 4 carbon atoms, R₂ is alkyl of 2 to 12 carbon cycloalkyl of 5 to 8 carbon atoms or aralkyl of 7 to 9 carbon atoms, G₁ has the same meaning as R₁, and G₂ and G₃ are independently branched alkyl of 3 to 12 carbon atoms, cycloalkyl of 5 to 8 carbon atoms or aralkyl of 7 to 9 carbon atoms, or one of G₂ and G₃ is methyl or ethyl when the other of G₂ and G₃ is branched alkyl, cycloalkyl or aralkyl as defined above, with a straight or branched chain alkene of 8 to 40 carbon atoms or mixture of said alkenes in the presence of an acidic catalyst at a temperature of 100° to 200° C.

Under these vigorous reaction conditions the alkylating agent (the alkene, straight or branched chain) itself undergoes a chemical transformation or isomerization. Accordingly the alkyl substituents introduced into the benzotriazole are not a single discrete moiety, but rather a random statistical mixture of isomeric groups. This random statistical mixture of groups (T₂ or T₃) represents a structural diversity which contributes to the liquid and non-crystalline physical state of the resulting products.

Under the instant process conditions the double bond in the alkene alkylating agent is isomerized along the carbon chain to give a random statistical mixture of moieties which can then be attached to the phenolic ring in the benzotriazole.

Illustrating with the alpha-olefin 1-octene, the random statistical mixture of octyl groups which would be included as T₂ or T₃ when T₂ or T₃ is octyl are

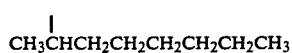

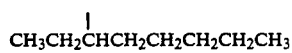

Thus T₂ or T₃ as octyl would lead to at least three isomers present in the mixture of benzotriazoles prepared.

Indeed, under the instant process conditions, the alkene being used in the instant process may fragment, dimerize or recombine in some fashion before reacting with the 2H-benzotriazole starting material. Such possibilities may in part account for the wide mixture of molecular species noted in the working Examples 1–11 where mass spectrographic analysis shows the presence of inter alia species with alkyl substituents having twice the number of carbon atoms as were present in the original alkene being used. In like manner, mass spectrographic anaylysis indicated some species with alkyl substituents having less than the number of carbon atoms in the alkene being used in the instant process or even having less than the number of carbon atoms in the alkyl groups in the original 2H-benzotriazle starting material used. In some cases, there were species having no alkyl substituents at all with complete dealkylation of the original 2H-benzotriazole having occurred. Inspection of the mass spectrographic analysis data shows that the combined amounts of all of these possible species enumerated in this paragraph are essentially minor components in the instant mixtures.

Although clearly the alkyl groups present in the instant mixtures are in an overwhelming degree present at the 3- and 5-positions (ortho and para positions) of the phenolic ring in the 2H-benzotriazoles of formula I, it cannot be ruled out that some substitution at the meta (4-) position or even in the benzo ring may not also occur in very minor and inconsequential amounts.

In the case where the starting 2H-benzotriazole has a lower alkyl substituent on the benzo ring as R₁ or G₁, said alkyl substituent is also unlikely to participate in the instant process since said benzo ring is quite deactivated and is not prone to direct alkylation and to participation in the instant process.

The alkenes useful in the instant process are any alkene whether straight or branched chain including alpha-olefins and alkenes having an internal double bond. During the instant alkylation process the double bond is isomerized along the carbon chain to give a random statistical mixture of alkenes which in turn produce for T₂ and T₃ a random statistical mixture of alkyl substituents.

Further contributing to the random statistical nature of the alkyl substituents for T₂ and T₃ is the fact that commercially available alkenes are often mixture of alkenes.

The preferred alkenes useful in the instant process are the alpha-olefins.

The alpha-olefins useful in this process are for example 1-octene, 1-nonene, 1-decene, 1-undecene, 1-dodecene, 1-tridecene, 1-tetradecene, 1-hexadecene, 1-octadecene, 1-eicosene, 1-docosene, 1-tetracosene or 1-triacontene.

These alpha-olefins are largely items of commerce or are made by the telomerization of ethylene by known methods.

Straight chain alkenes containing an internal double bond may be for example 2-octene, 4-octene, 5-decene or 9-tricosene.

These alkenes are also largely items of commerce.

The branched chain alkenes useful in this process are for example dipropylene, tripropylene, tetrapropylene, pentapropylene, diisobutylene, triisobutylene, tetraisobutylene, pentaisobutylene, 2,2,4,6,6-pentamethyl-3-heptene, diisoamylene, triisoamylene, tetraisoamylene or pentaisoamylene.

These highly branched alkenes are largely items of commerce or can be prepared from propylene, isobutylene or isoamylene by oligomerization with acid catalysts.

That this mixture of isomeric radicals as $T_2$ or $T_3$ is critical to obtaining a liquid or non-crystalline product may be seen from the fact that, when the alkyl substitution is a specific isomer, solid crystalline products are obtained. For example, 2-(2-hydroxy-3,5-di-tert-octylphenyl)-2H-benzotriazole melts at 105°-106° C.

The alkylation processes can be carried out over a range of conditions of time, temperature, olefin to benzotriazole ratios, catalysts and catalyst concentrations.

Sufficient time must be allowed for the alkylation to occur usually about 4 hours, but reaction times in excess of 12 hours do not increase yield of alkylated product. Preferably the alkylation reaction is carried out for a 6- to 8- hour period.

Relatively vigorous reaction conditions are needed since even the phenolic ring of the starting 2H-benzotriazole is deactivated. Reaction temperatures of 100° to 200° C. may be used. Temperatures below 140° C. give lower yields of alkylated product and temperatures in excess of 180° C. produce products of lesser quality and in lower yields. Preferably the process is carried out at 140° to 170° C., and most preferably at 160°-165° C. where yields in excess of 90% are obtained.

In order to alkylate the 2H-benzotriazole there must be at least 1 equivalent of alkene per equivalent of 2H-benzotriazole. Since competing reactions are also possible under these reactions conditions in respect to the alkene, such as dimerization, oligomerization or polymerization, yields of desired alkylated product are usually less than 40% when a 1:1 equivalent ratio of alkene:benzotriazole is used.

Increasing the concentration of alkene in respect to benzotriazole to a 4:1 equivalent ratio greatly increases yields of alkylated products to over 85%.

Larger excesses of alkene at a 6:1 equivalent ratio do not increase yields further.

Preferably the equivalent ratio of alkene:benzotriazole in the instant processes is 3.5 to 4.5:1.

The acidic catalyst is selected from the group consisting of aliphatic, aromatic and substituted aromatic sulfonic acids, sulfuric acid, phosphoric acid, acidic clays and heterogenous acidic catalysts (molecular sieves).

The concentration of catalyst useful in the instant process is 0.2 to 3 equivalents of catalyst per equivalent by benzotriazole, preferably 0.3 to 2 equivalents, and most preferably 0.5 to 1 equivalent of acid catalyst per equivalent of benzotriazole.

Examples of useful sulfonic acids are methanesulfonic acid, ethanesulfonic acid, butanesulfonic acid, benzenesulfonic acid, toluenesulfonic acid and dodecylbenzenesulfonic acid. Aliphatic sulfonic acids are preferable.

Commercially available acid activated clays such as Filtrol XJ-8303; Filtrol XJ-8405; Filtrol 22; Filtrol 4; and Filtrol 13 are also effective alkylation catalysts in the instant processes.

The most preferred catalyst is methanesulfonic acid.

The instant mixtures of formula I may be isolated following the alkylation reaction by a number of methods including the extraction procedures described in U.S. Pat. Nos. 4,587,346 and 4,675,352. Another facile method involves vacuum distillation at reduced pressure. The instant mixtures are usually distilled at temperatures in the range of 180°-210° C. at about 0.05 mm Hg.

Protection against damage caused by UV light is particularly important in photographic technology and especially in color photographic technology.

In order to protect the components (in particular dyes and couplers) present in a color photographic material as effectively as possible against destruction by ultraviolet light, UV absorbers are normally inserted into one or more of the upper layers of the material. This is effected as a rule by dissolving the UV-absorber in a high-boiling solvent and dispersing this solution, in the form of very fine droplets, in the appropriate coating solution. Since these droplets have a disadvantageous effect on the mechanical properties of the layer, and can "exude" if they are in the top layer of the material, it is important to keep the quantity of absorber solution as small as possible. This also makes it possible to produce thinner layers, which, in turn, offers advantages in processing (carry-over between baths and drying). It is therefore desirable to employ UV-absorbers which have as high a solubility as possible in the customary high-boiling solvents. The UV-absorbers of the state of the art, for example the stabilizers disclosed in Japanese Application Sho 54-95,233 do not, to a satisfactory extent, fulfil this requirement.

It has now been found that the instant products being liquid or non-crystalline can be used in color photographic material without the concomitant use of high-boiling solvents or with a very minimum amount thereof. Moreover, the instant compounds are essentially non-volatile and do not exude.

A typical photographic composition comprises a paper support on which are coated one or more light-sensitive layers and a layer containing the ultraviolet light absorber in a binder so placed as to protect the layer or layers requiring protection.

It is known that ultraviolet radiation has a detrimental effect on photographic layers. Ultraviolet radiation in light sources used for exposure of photographic products sometimes produces undesired exposure of the layer or layers of a photographic element. This is especially true in photographic elements designed for use in color photography in which the emulsion has been sensitized to the longer wavelength regions and it is desirable to record only the rays of the visible spectrum.

Color photographs on multilayer photographic material, particularly those in which the dye images are formed in sensitive emulsion layers by color development, are susceptible to fading and discoloration by the action of ultraviolet radiation to which the photographs are subjected during viewing. The residual couplers contained in the emulsion layer after the formulation of the picture images may be attacked by ultraviolet radiation resulting in an undersirable stain in the finished photograph. The action of ultraviolet radiation on finished color photographs is particularly noticeable on positive prints on paper or other opaque support since this type of print is frequently viewed in daylight which has a high content of ultraviolet radiation. The dye-fading and discoloration effects appear to be caused primarily by those wavelengths of light close to the visual region of the spectrum, i.e., 300–400 nm.

It is known that silver halide photographic materials can be protected from ultraviolet radiation by incorporating nondiffusing ultraviolet absorbing compounds in the silver halide emulsion layers or in overlying colloid coatings.

A large number of ultraviolet absorbers have been proposed for this use. Ultraviolet absorbing compounds for photographic use must generally be colorless or nearly colorless, show good compatability with the medium in which they are incorporated, be inert to other photographic addenda in the element and in the processing solution, must have good ultraviolet absorptivity and be stable to ultraviolet radiation. Representative compounds for incorporation in photographic elements are described for example, in U.S. Pat. No. 3,253,921.

Aromatic organic compounds such as ultraviolet absorbers, dye-forming couplers, antistain agents, filter dyes and the like to be effective must be nondiffusing and adequately distributed in highly dispersed form in the aqueous photographic gelatin layers.

This can be accomplished by a variety of chemical or physical techniques including the substitution of sulfonic acid or other solubilizing groups on the organic molecule; by use of a polar organic solvent imbibition procedures; or by solvent dispersion techniques.

The instant liquid or non-crystalline 2H-benzotriazoles are extremely useful as ultraviolet absorbers in photographic gelatin layers. They exhibit desirable absorption characteristics in the ultraviolet region, i.e., maximum absorption in the near ultraviolet and sharp cut-off just outside the visible region, are essentially colorless, are readily dispersed or dissolved by either the solvent-dispersion or imbibition methods, and are photographically inert.

The instant compounds exhibit excellent compatibility characteristics in the gelatin layers of the photographic composition which lead to compositions essentially without haze coupled with superior protection of the color dye images against the harmful effects of ultraviolet radiation. This combination of properties clearly distinguishes the instant benzotriazole light absorbers from the generic disclosure of U.S. Pat. No. 3,253,921. These salubrious results are obtained when the instant benzotriazoles are incorporated directly into the gelatin layer or by the solvent dispersion technique.

An object of the invention is to provide novel photographic elements protected against the harmful effects of ultraviolet radiation by incorporation of ultraviolet absorbing materials. Another object is to provide photographic color materials containing ultraviolet absorbers incorporated in a highly stable form. A further object is to provide a non-diffusing ultraviolet absorber.

The invention relates further to stabilized organic material which is in the form of photographic material or is part of a photographic material, the photographic material containing, preferably in top layers, 0.05 to 5% by weight, relative to the photographic material without stabilizer, of a compound according to the invention.

When the instant compounds are liquid, the instant benzotriazoles are incorporated into a hydrophilic colloid by heating an aqueous solution of said hydrophilic colloid containing the liquid benzotriazole and an appropriate dispersing agent to a moderate temperature above the easy flow point of the instant benzotriazole, agitating the resulting mixture to obtain a fine dispersion of the benzotriazole in the colloid, and then cooling the mixture.

When the instant compounds are not liquid at room temperature, but are non-crystalline, the use of a minimum amount of high-boiling solvent to assist in getting the instant compound to flow is contemplated to achieve the above objects by the solvent dispersion technique to incorporate the instant compounds in aqueous hydrophilic colloid solutions for coating silver halide emulsion layers or associated hydrophilic colloid layers.

The preferred high-boiling solvents include di-n-butyl phthalate, benzyl phthalate, triphenyl phosphate, tri-o-cresyl phosphate, diphenyl mono-p-tert-butylphenyl phosphate, monophenyl di-p-tert-butylphenyl phosphate, diphenyl mono-o-chlorophenyl phosphate, monophenyl di-o-chlorophenyl phosphate, tri-p-tert-butylphenyl phosphate, tri-o-phenylphenyl phosphate, di-p-tert-butylphenyl mono(5-tert-butyl-2- phenylphenyl) phosphate, etc.

The hydrophilic colloids or binders advantageously include gelatin, albumin, etc., cellulose derivatives, polyvinyl compounds, etc. The polymeric binders include polyvinyl alcohol or a hydrolyzed polyvinyl acetate; a far hydrolyzed cellulose ester such as cellulose acetate hydrolyzed to an acetyl content of 19-26 percent; a water-soluble ethanolamine cellulose acetate, a polyacrylamide having a combined acrylamide content of 30-60 percent and a specific viscosity of 0.25-1.5 or an imidized polyacrylamide of like acrylamide content and viscosity; a vinyl alcohol polymer containing urethane carboxylic acid groups; or containing cyanoacetyl groups such as the vinyl alcohol/vinyl cyanoacetate copolymer; or a polymeric material which results from polymerizing a protein or a saturated acylated protein with a monomer having a vinyl group.

The dispersion of an instant compound in the binder material is coated over the light-sensitive layer of the photographic element. Where the photographic element is a material intended for use in color photography, the ultraviolet filter layer need not be an outer layer, but can be used as an interlayer, i.e., under the layer or layers not needing the protection and over the layer or layers needing protection. For example, in a multilayer material comprising three differentially sensitized layers, the red-sensitive layer being adjacent to the support, the green-sensitive layer being superimposed on the red-sensitive layer and the blue-sensitive layer being outermost with respect to the other light-sensitive layers, the ultraviolet filter layer can be placed between the blue and green-sensitive layers or between the green and red-sensitive layers. Similarly, in another photographic element in which the layers are reversed, that is, the blue-sensitive layer is coated over the support, and the green and red-sensitive layers are superposed over the blue-sensitive layer in that order, the ultraviolet filter layer can be over all three layers or between any two of the layers. Alternatively, the ultraviolet absorbing composition can be incorporated directly in the light-sensitive emulsion instead of, or in addition, being present in another layer. The amount of the ultraviolet absorbing material used can be varied, depending upon the effect desired and the use that will be made of the material.

The ultraviolet absorbing compositions are coated over a wide range of concentrations; usually they are coated in the range of from 20 to 300 mg. of ultraviolet absorbing compound per ft.$^2$ photographic element. A preferred range is from 75 to 160 mg/ft.$^2$. The optimum coating concentrations will depend upon the particular photographic element to be protected and the amount of protection desired. The optimum coating concentrations for a given photographic element can be determined by methods well known in the art.

Any photographic element may be advantageously protected according to the invention. These photographic elements may have as their support any of the conventional support materials, such as firm supports, e.g., cellulose acetate, etc. opaque supports, such as white pigmented film, paper and the like.

The instant ultraviolet absorbing compounds are characterized by their non-diffusibility in coated layers, good stability in the incorporating solvents and their good ultraviolet absorption. Ultraviolet absorbing layers containing the instant compounds incorporated according to the preferred methods of the invention have unexpectedly excellent stability upon prolonged exposure to ultraviolet radiation which makes them ideally suited for protecting photographic elements, particularly dye images in color materials.

The instant liquid benzotriazoles may be used advantageously in photographic elements with other liquid ultraviolet absorbers (UVA) such as 5-chloro-2-[2-hydroxy-3-tert-butyl-5-(2-octyloxyethyl)-phenyl]-2H-benzotriazole.

The instant liquid benzotriazoles are also useful as solvents for other solid UVA materials or for other components in a silver halide photographic element when used alone or in combination with common photographic oils as described in European Pat. Application Nos. 84,692 and 84,694.

Such other components include
yellow, magenta and cyan couplers
DIR couplers, black couplers, colorless couplers
chromogenic coupler stabilizers
chromogenic dye stabilizers
accutance dyes, antihalation dyes, dye-bleach dyes
formaldehyde scavengers
sensitizing dyes
optical brightening agents
oxidized developer scavengers
compounds which release diffuseable dyes on development
electron transfer agents Examples of other UVA materials which may be used in combination with the instant compounds include 1. Benzophenones 2,4-dihydroxy-benzophenone
2-hydroxy-4-ethoxy-benzophenone
2,2'-dihydroxy-4-methoxy-benzophenones
2-hydroxy-4-n-octoxy-benzophenone
2-hydroxy-4-isooctoxy-benzophenone
2-hydroxy-4-dodecyloxy-benzophenone 2. Benzotriazoles 2-(2-hydroxy-5-methylphenyl)-benzotriazole,
2-(2-hydroxy-3,5-di-t-butylphenyl)-benzotriazole,
2-(2-hydroxy-3-t-butyl-5-ethylphenyl)-5-chlorobenzotriazole,
2-(2-hydroxy-3,5-di-t-butylphenyl)-5-chlorobenzotriazole,
2-(2-hydroxy-3,5-di-tert-amylphenyl)-benzotriazole,
2-(2-hydroxy-3-s-butyl-5-t-butylphenyl)-benzotriazole,
2-(2-hydroxy-5-t-butylphenyl)-benzotriazole,
2-(2-hydroxy-5-t-octylphenyl)-benzotriazole, a mixture of 50% of 2-[(2-hydroxy-3-t-butyl-5-((2'''-n-octoxycarbonyl)-ethyl)phenyl]-5-chlorobenzotriazole and 50% of 2-[(2-hydroxy-3-t-butyl-5-((2''-ethylhexyloxy)carbonyl)ethyl)phenyl]-5-chlorobenzotriazole,
2-[2-hydroxy-3,5-di-(alpha,alpha-dimethylbenzyl)-phenyl]-benzotriazole 3. Benzylidene malonates methyl 2-carboxymethyl-3-(4'-methoxyphenyl)-acrylate 4. Salicylates p-octylphenyl salicylate
phenyl salicylate
t-butylphenyl salicylate 5. Monobenzoates Resorcinol monobenzoate
3,5-di-t-butyl-4-hydroxybenzoic acid hexadecyl ester 6. Oxamides 5-t-butyl-2-ethoxy-2'2'-ethyloxanilide,
2-ethoxy-2'-ethyloxanilide 7. 5-dialkylamino-2,4-pentadienoic acid esters 5-diethylamino-2-phenylsulphonyl-2,4-pentadienoic acid hendecylester 8. 5-dialkylamino-2-cyano-2,4-pentadiene nitriles 5-dihexylamino-2-cyano-2,4-pentadiene nitrile 9. 2,4-di-t-butylphenyl 3,5-di-t-butyl-4-hydroxybenzoate, 3,5-ditertieary-butyl-p-hydroxy-benzoic acid,
di(1,2,2,6,6-pentamethyl-4-piperidinyl)-butyl (3',5'-di-t-butyl-4-hydroxybenzyl)malonate,
bis(1,2,6,6-tetramethyl-4-piperidinyl) sebacate,
bis(1,2,2,6,6-pentamethyl-4-piperidyl) sebacate,
butane tetracarboxylic acid tetra(2,2,6,6-tetramethyl-4-piperidinyl)ester The instant compounds may also be used in cyan layers together with either phenol, naphthol or 2,5-diacylaminophenol couplers or mixtures of these couplers to prevent image fading and discoloration.

The use of known benzotriazoles in such systems is described in Japanese Kokai Sho 58-221,844 and 59-46,646.

The compounds of this invention are effective light stabilizers in a wide range of organic polymers. Polymers which can be stabilized include:

1. Polymers which are derived from mono- or diolefins e.g., polyethylene which can optionally be cross-linked, polypropylene, polyisobutylene, polymethylbutene-1, polymethylpentene-1, polyisoprene, polybutadiene.

2. Mixtures of the homopolymers cited under 1), for example mixtures of polypropylene and polyethylene, polypropylene and polybutene-1, polypropylene and polyisobutylene, 3. Copolymers of the monomers based on the homopolymers cited under 1), for example ethylene/propylene copolymers, propylene/butene-1 copolymers, propylene/iso-butylene copolymers, ethylene/butene-1 copolymers as well as terpolymers of ethylene and propylene with a diene, for example hexadiene, dicyclopentadiene or ethylidene norbornene, and copolymers of alpha-olefins, e.g., ethylene with acrylic or methacrylic acid, and blends of such copolymers with homopolymers described in paragraphs1 and 2 above.

4. Polystyrene.

5. Copolymers of styrene and of alpha-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well a block copolymers, e.g., styrene/- butadiene/styrene, styrene/isoprene/styrene and styrene/ethylenepropylene/ styrene block copolymers.

6. Graft copolymer of styrene, for example the graft polymer of tyrene to polybutadiene, the graft polymer of styrene with acrylonitrile to polybutadiene as well as mixtures thereof with the copolymers cited under 5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Linear and crosslinked polymers which are derived from alpha,beta-unsaturated acids and derivatives thereof, such as amides and polyacrylonitrile.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Hompolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polybutylene oxide.

13. Polyphenylene oxides, and blends of polyphenylene oxides with impact resistant polystyrene.

14. Polyurethanes and polyureas, such as in urethane coatings.

15. Polycarbonates.

16. Polysulfones.

17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenylene-isophthalamide.

18. Polyesters which are derived from dicarboxylic acids and dialcohols and/or from hydroxycarboxylic acids or the corresponding lactones, for example polyethylene glycol terephthalate, poly-1,4-dimethylol-cyclohexane terephthalate.

19. Cross-linked polymers which are derived from aldehydes on the one hand and from phenols, ureas and melamine on the other, for example phenol/formaldehyde, urea/formaldehyde and melamine/formaldehyde resin.

20. Alkyd resins, for example glycerol/phthalic acid resins and mixtures thereof with melamine/formaldehyde resins.

21. Unsaturated polyesters reins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methyl cellulose.

The stabilizing of polyolefins, styrene polymers, polyacrylates, polyamides, polyurethanes, halogen containing vinyl polymers, alkyd resins, thermoset acrylic resins, and epoxy resins is of particular importance, and the instant benzotriazole mixtures are outstandingly suitable for this purpose. Examples of such polymers are high density and low density polyethylene, polypropylene, ethylene/propylene copolymers, polystyrene, styrene block copolymers, halogen containing vinyl polymers, linear (=thermoplastic) and crosslinked (=thermoset) polyacrylates and polyurethanes, alkyd resins and epoxy resins in the form of coatings, lacquers, filaments, films, sheets, adhesives, elastomers, foams or shaped articles.

The instant stabilizers are added to the substrates in a concentration of 0.05 to 10% by weight, calculated relative to the material to be stabilized. Preferably, 0.1 to 5% by weight of the stabilizer calculated relative to the material to be stabilized, is incorporated into the latter.

Incorporation can be effected after polymerization, for example by mixing the compounds and, if desired, further additives into the melt by the methods customary in the art, before or during shaping, or by applying the dissolved or dispersed compounds to the polymer, with subsequent evaporation of the solvent if necessary.

The stabilizers can also be added to the substrates to be stabilized in the form of a master batch which contains these compounds, for example in a concentration of 2.5 to 25% by weight.

Although the compounds of the invention may be used to provide a light stabilizing function, the compounds of this invention are often combined with other stabilizers, even other light stabilizers, in the preparation of stabilized compositions. The stabilizers may be used with phenolic antioxidants, pigments, colorants or dyes, light stabilizers such as hindered amines, metal deactivators, etc.

In general, the stabilizers of this invention are employed from about 0.05 to about 10% by weight of the stabilized composition, although this will vary with the particular substrate and application. An advantageous range is from about 0.1 to about 5%.

The stabilizers of Formula I or II may readily be incorporated into the organic substrates by conventional techniques, at any convenient stage prior to the manufacture of shaped articles therefrom. For example, the stabilizer may be mixed with the dry polymer, or a suspension, solution or emulsion of the stabilizer may be mixed with a solution, suspension, or emulsion of the polymer. The stabilized polymer compositions of the invention may optionally also contain from about 0.05 to about 10%, preferably from about 0.1 to about 5%, by weight of various conventional additives, such as the following, particularly phenolic antioxidants or light-stabilizers, or mixtures thereof:

1 Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as for example, 2,5-di-tert.-butyl-hydroquinone, 2,5-di-tert.-amyl-hydroquinone, 2,6-di-tert.-butyl-hydroquinone, 2,5-di-tert.-butyl-4-hydroxy-anisole, 3,5-di-tert.- butyl-4-hydroxy-anisole, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as for example, 2,2'-thio-bis-(6-tert.-butyl-4-methylphenol), 2,2'-thio-bis-(4-octylphenol), 4,4'-thio-bis-(tert.-butyl-33-methylphenol), 4,4'-thio-bis-(3,6-di-sec.-amyl-phenol), 4,4'-thio-bis-(6-tert.-butyl-2-methylphenol) and 4,4'-bis-(2,6-dimethyl-4-hydroxyphenyl) disulfide.

1.4 Alkylidene-bisphenols, such as, for example, 2,2'-methylene-bis-(6-tert.-butyl-4-methylphenol), 2,2'-methylene-bis-(6-tert.butyl-4-ethylphenol), 4,4'-methylene-bis-(6-tert.-butyl-2-methylphenol), 4,4'-methylene-bis-(2,6-di-tert.-butylphenol), 2,6-di-(3-tert.-butyl-5-methyl-2-hydroxybenzyl)-4-(methylphenol, 2,2'-methylene-bis-[4-methyl-6-(alpha-methylcyclohexyl)-phenol], 1,1-bis(3,5-dimethyl-2-hydroxyphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecyl-mercapto-butane, 1,1,5,5-tetra-(5-tert.-butyl-4-hydroxy-2-methylphenyl)-pentane and ethylene glycol bis-[3,3-bis-(3-tert.-butyl-4-hydroxyphenyl)-butyrate].

1.5 O-, N- and S-benzyl compounds, such as for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl]2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethyl-benzene, 1,4-di-(3,5-di-tert-butyl-4-hydroxybenzyl)-2,3,5,6-tetramethylbenzene and 2,4,6-tri-(3,5-di-tert.-butyl-4-hydroxy-benzyl)-phenol.

1.8 s-Triazine compounds, such as, for example 2,4-bis-octylmercapto-6-(3,5-di-tert.-butyl-4-hydroxy-anilino)-s-triazine, 2-octylmercapto-4,6-bis-(3,5-di-tert.-butyl-4-hydroxy-anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxphenylethyl)-s-triazine and 1,3,5-tris-(3,5-di-tert.-butyl-4-hydroxybenzyl) isocyanurate.

1.9 Amides of β-(3,5-di-tert.-butyl-4-hydroxyphenyl)-propionic acids, such as, for example 1,3,5-tris-(3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine, N,N'-bis-β-(3,5-di-t-butyl-4-hydroxyphenyl)-propionyl-hydrazine.

1.10 Esters of β-(3,5-di-tert.-butyl-4-hydroxyphenyl)-propionic acid with monohydric or polyhydric alcohols, such as for example, with methanol, ethanol, octadecanol, 1,6-hexanediol; 1,9-nonanediol, ethylene glycol, 1,2-propane-diol, diethylene glycol, thiodiethylene glycol, neopentyl glycol, pentaerythritol, 3-thiaundecanol, 3-thia-pentadecanol, trimethylhexanediol, trimethyl- olethane, trimethylolpropane, tris-hydroxyethyl isocyanurate and 4-hydroxymethyl-1-phospha-2,6,7-trioxabicyclo-[2.2.2]octane.

1.11 Esters of β-(5-tert.-butyl-4-hydroxy-3-methylphenyl)-propionic acid with monohydric or polyhydric alcohols, such as for example, with methanol, ethanol, octadecanol, 1,6-hexanediol, 1,9-nonanediol, ethylene glycol, 1,2-propanediol, di-ethylene glycol, thiodiethylene glycol, neopentyl glycol, pentaerythritol, 3-thiaundecanol, 3-thia-pentadecanol, trimethylhexanediol, trimethylole- ethane, trimethylolpropane, tris-hydroxyethyl isocyanurate and 4-hydroxymethyl-1-phospha-2,6,7-trioxabicyclo[2.2.2]- octane.

1.12 Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, neopentyl glycol, pentaerythritol, 3-thia-undecanol, -thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2.2.2]-octane, especially the tetrakis ester of pentaerythritol.

1.13 Benzylphosphonates, such as, for example, dimethyl 2,5-di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

2. Light-stabilizers 2.1 Esters of optionally substituted benzoic acids, e.g., 3,5-di-tert.-butyl-4-hydroxybenzoic acid, 2,4-di-tert.-butyl-phenyl ester or -octadecyl ester or 2-methyl-4,6-di-tert.-butyl-phenyl ester.

2.2 Sterically hindered amines e.g.., 4-benzoyl-2,2,6,6-tetramethylpiperidine, 4-stearyloxy-2,2,6,6-tetramethyl-piperidine, bis-(2,2,6,6-tetramethylpiperidyl) sebacate, bis-(1,2,2,6,6-pentamethylpiperidyl) sebacate, bis-(1,2,2,6,6-pentamethylpiperidyl) 2-n-butyl-2-(2-hydroxy-3,5-di-tert-butyl-benzyl)malonate or 3-n-octyl-7,7,9,9-tetra-methyl-1,3,8-triazaspiro[4.5]decane-2,4-dione.

2.3 Oxalic acid diamides, e.g., 4,4'-di-octyloxy-oxanilide, 2,2'-di-octyloxy-5,5'-di-tert.butyl-oxanilide, 2,2'-didodecycloxy-5,5'-di-tert.-butyl-oxanilide, 2-ethoxy-2'-ethyl-oxanilide, N,N'-bis-(3-dimethyl-aminopropyl)-oxalimide, 2-ethoxy-5-tert.-butyl-2'-ethyl-oxanilide and the mixture thereof with 2-ethoxy-2'-ethyl-5,4'-di-tert.-butyl-oxanilide, or mixture of ortho- and paramethoxy- as well as of o- and p-ethoxy-di-substituted oxanilides.

3. Metal deactivators, e.g., oxanilide, isophthalic acid dihydrazide, sebacic acid-bis-phenylhydrazide, bis-benzylidene-oxalic acid dihydrazide, N,N'-diacetal-adipic acid dihydrazide, N,N'-bis-salicycloyl-oxalic acid dihydrazide, N,N'-bis-salicyloylhydrazine, N,N'-bis-(3,5-di-tert.-butyl-4-hydroxy-phenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

4. Basic co-stabilizers, e.g., alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites and phosphonites, such as, for example, triphenyl phosphite, diphenylalkyl phosphites, phenyldialkyl phosphites, tri-(nonyl-phenyl) phosphite, trilauryl phosphite, trioctadecyl phosphite and 3,9-isodecyloxy-2,4,8,10-tetraoxa-3,9-diphospha-[5.5]-undecane and tetra(2,4-di-tert-butylphenyl) diphenylene-4,4'-bis(phosphonite).

Other additives that can be incorporated in the stabilized compositions are thiosynergists such as dilauryl thiodipropionate, lubricants such as stearyl alcohol, fillers, asbestos, kaolin, talc, glass fibers, pigments, optical brighteners, flameproofing agents and antistatic agents.

The following examples are presented for the purpose of illustration only and are not to be construed to limit the nature or scope of the instant invention in any manner whatsoever.

EXAMPLES 1–11

In a flask fitted with a nitrogen blanket, stirrer, reflux condenser and addition funnel, 0.5 mole of olefin, 0.5 mole of the 2H-benzotriazole and 0.5 mole of 98% methanesulfonic acid are heated to 160° C. and held at this temperature for a period of four hours during which time an additional 1.5 moles of olefin are added to the reaction mixture.

The mixture is then cooled to 20° C. The lower methanesulfonic acid layer is separated off and the upper olefin-product layer is washed once with 1000 ml of 2% sodium carbonate solution and finally dried over anhydrous magnesium sulfate.

The dried organic solution is vacuum stripped at 170° C./0.5 mm Hg to remove the unreacted olefin. The residual material is then vacuum distilled on a Kugelrohr column to give a fraction boiling at about 170°–180° C./0.1 mm Hg which includes some hydrocarbon material and the desired at about 180°–210° C./0.05 mm Hg. The desired products boiling products are in every case viscous yellow liquids.

The products prepared by the method described above are analyzed by chemical ionization mass spectrometry using a direct probe inlet. Control samples of the various starting materials confirm that the observed product distributions are real and are not artifacts due to fragmentation inside the mass spectrometer.

| Example | Starting 2H-benzotriazole | | | Olefin |
|---|---|---|---|---|
| | $R_2$ | $G_2$ | $G_3$ | |
| 1 | tert-butyl | — | — | n-dodecene |
| 2 | tert-amyl | — | — | n-dodecene |
| 3 | tert-octyl | — | — | n-dodecene |
| 4* | tert-octyl | — | — | n-dodecene |
| 5 | alpha,alpha-dimethylbenzyl (= cumyl) | — | — | n-dodecene |
| 6 | — | tert-butyl | tert-butyl | n-dodecene |
| 7 | — | tert-amyl | tert-amyl | n-dodecene |
| 8 | — | tert-octyl | tert-octyl | n-dodecene |
| 9 | — | cumyl | cumyl | n-dodecene |
| 10 | tert-octyl | — | — | propylene tetramer |
| 11 | ethyl | — | — | n-dodecene |

*Reaction is run with 1 mole of olefin, 1 mole of 2H-benzotriazole and 0.5 mole of methanesulfonic acid.

The mass spectrometer analyses of the reaction products obtained from Examples 1–11 are given on Tables 1–11 below.

Tables 1–5 and 10–11 give the results of reacting an olefin with a 2-(2-hydroxy-5-alkyl(or cumyl)phenyl)-2H-benzotriazole. Tables 6–9 show the results of reacting an olefin with a 2-(2-hydroxy-3,5-di-tert-alkyl(or cumylphenyl)-2H-benzotriazole.

In Tables 1–5 and 10–11, the "normal" products which would be obtained by olefin addition to the 2H-benzotriazole without any displacement, fragmentation or other reaction are asterisked. Such products usually amount to much less than 50% of the product mixture.

In Tables 6–9, The products obtained by an alkyl exchange reaction where one alkyl (or cumyl) is replaced by a dodecyl moiety are asterisked. Such products occur in the 10–36% range of the final product mixture.

TABLE 1

ALKYLATION OF 2-(2-HYDROXY-5-tert-BUTYLPHENYL)-2H-BENZOTRIAZOLE WITH n-DODECENE COMPOSITION ANALYSIS

| Molecular Weight | Total Carbon Atoms in Alkyl Substituent(s) | Proportion in bp 170°/0.1 mm Hg Fraction** (in %) | Proportion in by 180–210°/0.05 mm Hg Fraction (in %) | Comments |
|---|---|---|---|---|
| 267 | $C_4$ | 6 | 1 | |
| 323 | $C_8$ | 3 | 1 | |
| 337 | $C_9$ | 4 | | |
| 379 | $C_{12}$ | 32 | 40 | $C_{12}$ only |
| 435 | $C_{16}$ | 40* | 50* | $C_4 + C_{12}$ |
| 491 | $C_{20}$ | 5 | 4 | |
| 547 | $C_{24}$ | 2 | 1 | $2 \times C_{12}$ or $C_{24}$ |

**This fraction includes hydrocarbons.

TABLE 2

ALKYLATION OF 2-(2-HYDROXY-5-tert-AMYLPHENYL)-2H-BENZOTRIAZOLE WITH n-DODECENE COMPOSITION ANALYSIS

| Molecular Weight | Total Carbon Atoms in Alkyl Substituent(s) | Proportion in bp 180–210°/0.06 mm Hg Fraction (in %) | Comments |
|---|---|---|---|
| 281 | $C_5$ | 6 | |
| 337 | $C_9$ | 2 | |
| 351 | $C_{10}$ | 2 | |
| 379 | $C_{12}$ | 36 | $C_{12}$ only |
| 421 | $C_{15}$ | 3 | |
| 435 | $C_{16}$ | 4 | |
| 449 | $C_{17}$ | 38* | $C_{12} + C_5$ |
| 491 | $C_{20}$ | 2 | |
| 505 | $C_{21}$ | 2 | |

TABLE 3

ALKYLATION OF 2-(2-HYDROXY-5-tert-OCTYLPHENYL)-2H-BENZOTRIAZOLE WITH n-DODECENE COMPOSITION ANALYSIS

| Molecular Weight | Total Carbon Atoms in Alkyl Substituent(s) | Proportion in bp 170°/0.1 mm Hg Fraction (in %) | Proportion in by 180°/0.03 mm Hg Fraction (in %) | Comments |
|---|---|---|---|---|
| 267 | $C_4$ | 8 | | |
| 281 | $C_5$ | 3 | | |
| 323 | $C_8$ | 11 | 4 | starting material or isomers |
| 337 | $C_9$ | 5 | 2 | |
| 351 | $C_{10}$ | 3 | 2 | |
| 365 | $C_{11}$ | 4 | 4 | |
| 379 | $C_{12}$ | 30 | 37 | $C_{12}$ only |
| 393 | $C_{13}$ | 3 | 3 | |
| 421 | $C_{15}$ | | 5 | |
| 435 | $C_{16}$ | 9 | 13 | $C_4 + C_{12}$ |
| 491 | $C_{20}$ | 18* | 23* | $C_8 + C_{12}$ |
| 547 | $C_{24}$ | 3 | 3 | $2 \times C_{12}$ |

TABLE 4

ALKYLATION OF 2-(2-HYDROXY-5-tert-OCTYLPHENYL)-
2H-BENZOTRIAZOLE WITH n-DODECENE
COMPOSITION ANALYSIS

| Molecular Weight | Total Carbon Atoms in Alkyl Substituents | Proportion in bp 140-70° Fraction 2-10 mm Hg (in %) | Proportion in in Fraction bp 170-180° C. 0.05 mm Hg (in %) | Proportion overall Proportion overall calcd. (in %) | Comments |
|---|---|---|---|---|---|
| 211 | 0 | 10.6 | — | 8.1 | Fully de-alkylated product |
| 267 | $C_4$ | 23.5 | 0.5 | 18.1 | |
| 323 | $C_8$ | 41 | 24.6 | 37.2 | Starting material and/or isomers |
| 365 | $C_{11}$ | 3.7 | 3.1 | 3.5 | |
| 379 | $C_{12}$ | 14.7 | 27.4 | 17.6 | Loss of $C_8$ and Addition of $C_{12}$ |
| 421 | $C_{15}$ | 1.0 | 2.5 | | |
| 435 | $C_{16}$ | 2.0 | 8.7 | 3.5 | |
| 491 | $C_{20}$ | 1.5* | 20.6* | 5.9* | $C_8 + C_{12}$ "normal product" |
| 547 | $C_{24}$ | 0.1 | 2.3 | 0.6 | $2 \times C_{12}$ |

TABLE 5

ALKYLATION OF 2-(2-HYDROXY-5-CUMYLPHENYL)-2H-BENZOTRIAZOLE
WITH n-DODECENE
COMPOSITION ANALYSIS

| Molecular Weight | Total Carbon Atoms in Alkyl Substituent(s) | Proportion in bp by 180-210°/.04 mm Hg Fraction (in %) | Comments |
|---|---|---|---|
| 379 | $C_{12}$ | 73 | $C_{12}$ only |
| 421 | $C_{15}$ | 6 | |
| 435 | $C_{16}$ | 4 | |
| 497 | $C_{21}$ | 12* | $C_{12}$ + Cumyl |
| 547 | $C_{24}$ | 5 | |

TABLE 6

ALKYLATION OF 2-(2-HYDROXY-3,5-DI-tert-BUTYLPHENYL)-2H-BENZOTRIAZOLE
WITH n-DODECENE
COMPOSITION ANALYSIS

| Molecular Weight | Total Carbon Atoms in Alkyl Substituent(s) | Proportion in bp 160°/1.0 mm Hg Fraction (in %) | Proportion in by 190-202°/.01 mm Hg Fraction (in %) | Comments |
|---|---|---|---|---|
| 211 | 0 | 2 | — | |
| 267 | $C_4$ | 5 | 1 | |
| 323 | $C_8$ | 5 | 2 | |
| 337 | $C_9$ | 4 | 1 | |
| 351 | $C_{10}$ | 2 | 1 | |
| 365 | $C_{11}$ | 3 | 3 | |
| 379 | $C_{12}$ | 35 | 44 | $C_{12}$ only |
| 393 | $C_{13}$ | 3 | 2 | |
| 435 | $C_{16}$ | 28* | 36* | $C_4 + C_{12}$ |
| 491 | $C_{20}$ | 6 | 7 | |
| 547 | $C_{24}$ | 3 | 2 | |

TABLE 7

ALKYLATION OF 2-(2-HYDROXY-3,5-DI-tert-AMYLPHENYL)-2H-BENZOTRIAZOLE
WITH n-DODECENE
COMPOSITION ANALYSIS

| Molecular Weight | Total Carbon Atoms in Alkyl Substituent(s) | Proportion in by 180-205°/.05 mm Hg Fraction (in %) |
|---|---|---|
| 337 | $C_9$ | 1 |
| 351 | $C_{10}$ | 2 |
| 379 | $C_{12}$ | 42 |
| 393 | $C_{13}$ | 3 |
| 435 | $C_{16}$ | 11 |
| 449 | $C_{17}$ | 35* |
| 491 | $C_{20}$ | 3 |
| 547 | $C_{24}$ | 2.5 |

TABLE 8

ALKYLATION OF 2-(2-HYDROXY-3,5-DI-tert-OCTYLPHENYL)-2H-BENZOTRIAZOLE
WITH n-DODECENE
COMPOSITION ANALYSIS

| Molecular Weight | Total Carbon Atoms in Alkyl Substituent(s) | Proportion in bp 185-202°/.06 mm Hg Fraction (in %) | Comments |
|---|---|---|---|
| 267 | $C_4$ | 2 | |
| 281 | $C_5$ | 1 | |
| 309 | $C_7$ | 2 | |
| 323 | $C_8$ | 12 | $C_{12}$ only |
| 337 | $C_9$ | 2 | |
| 351 | $C_{10}$ | 1 | |
| 365 | $C_{11}$ | 3 | $C_{12} + C_5$ |
| 379 | $C_{12}$ | 17 | |
| 435 | $C_{16}$ | 46 | $C_{12} + C_4$ and/or $C_8 + C_8$ |
| 491 | $C_{20}$ | 10* | |
| 547 | $C_{24}$ | 1 | |

TABLE 9

ALKYLATION OF 2-(2-HYDROXY-3,5-DICUMYLPHENYL)-2H-BENZOTRIAZOLE
WITH n-DODECENE
COMPOSITION ANALYSIS

| Molecular Weight | Total Carbon Atoms in Alkyl Substituent(s) | Proportion in bp 180-210°/0.05 mm Hg Fraction (in %) | Comments |
|---|---|---|---|
| 211 | 0 | 1 | Fully de- |

TABLE 9-continued
ALKYLATION OF 2-(2-HYDROXY-3,5-DICUMYLPHENYL)-2H-BENZOTRIAZOLE WITH n-DODECENE COMPOSITION ANALYSIS

| Molecular Weight | Total Carbon Atoms in Alkyl Substituent(s) | Proportion in bp 180–210°/ 0.05 mm Hg Fraction (in %) | Comments |
|---|---|---|---|
|  |  |  | alkylated product |
| 323 | $C_8$ | 1 |  |
| 365 | $C_{11}$ | 1 |  |
| 379 | $C_{12}$ | 72 | $C_{12}$ only |
| 435 | $C_{16}$ | 3 |  |
| 497 | $C_{21}$ | 20* | $C_{12}$ + cumyl |

TABLE 10
ALKYLATION OF 2-(2-HYDROXY-5-tert-OCTYLPHENYL)-2H-BENZOTRIAZOLE WITH PROPYLENE TETRAMER COMPOSITION ANALYSIS

| Molecular Weight | Total Carbon Atoms in Alkyl Substituent(s) | Proportion in bp 200–210°/ 0.05 mm Hg Fraction (in %) | Comments |
|---|---|---|---|
| 365 | $C_{11}$ | 4 |  |
| 379 | $C_{12}$ | 14 | $C_{12}$ only |
| 393 | $C_{13}$ | 5.5 |  |
| 407 | $C_{14}$ | 5 |  |
| 421 | $C_{15}$ | 7.5 |  |
| 435 | $C_{16}$ | 13 | $C_{12}$ + $C_4$ |
| 449 | $C_{17}$ | 8 |  |
| 463 | $C_{18}$ | 7 |  |
| 477 | $C_{19}$ | 8 |  |
| 491 | $C_{20}$ | 13* | $C_{12}$ + $C_8$ |
| 505 | $C_{21}$ | 5.5 |  |
| 519 | $C_{22}$ | 3.5 |  |
| 547 | $C_{24}$ | 4.5 |  |

TABLE 11
ALKYLATION OF 2-(2-HYDROXY-5-ETHYLPHENYL)-2H-BENZOTRIAZOLE WITH n-DODECENE COMPOSITION ANALYSIS

| Molecular Weight | Total Carbon Atoms in Alkyl Substituent(s) | Proportion in bp 180–210°/ 0.06 mm Hg Fraction (in %) | Comments |
|---|---|---|---|
| 239 | $C_2$ | 8.0 |  |
| 267 | $C_4$ | 1.5 |  |
| 281 | $C_5$ | 1.5 |  |
| 295 | $C_6$ | 2.6 |  |
| 309 | $C_7$ | 1.9 |  |
| 323 | $C_8$ | 1.6 |  |
| 351 | $C_{10}$ | 2.1 |  |
| 379 | $C_{12}$ | 6.2 | $C_{12}$ only |
| 407 | $C_{14}$ | 62.7* | $C_{12}$ + $C_2$ |
| 433 | $C_{16}$ | 4.0 |  |
| 449 | $C_{17}$ | 4.1 |  |
| 463 | $C_{18}$ | 3.8 |  |
| 547 | $C_{24}$ | 0.2 |  |
| 575 | $C_{26}$ | 0.9 |  |

EXAMPLE 12

To a 1-liter reaction flask fitted with a nitrogen blanket, stirrer, dosing device with proportion pump and distillation column connected with a condensation trap and water jet vacuum pump is charged 323 grams (1 mol) of 2-(2-hydroxy-3,5-di-tert-butylphenyl)-2H-benzotriazole and 96.1 grams (1 mol) of methanesulfonic acid. The reaction flask is swept with nitrogen. Then, without stirring, the mixture is melted by heating to about 150° C. Heating is now continued with stirring to a temperature of 175° C. At this temperature, 234 grams (1.02 mol) of n-hexadecene are added below the surface of the mixture through the dosing device over a 6-hour period. The reaction mixture is then heated for another 30 minutes at 175° C. The mixture is then cooled to about 95° C. and extracted with 100 ml of water, 100 ml of 4% sodium bicarbonate solution and again with 100 ml of water. Then, 100 grams of bleaching earth (Prolith Rapid) are added and the water is distilled off at 100° C./20 mbar. The bleaching earth is removed by filtration to give 532 grams (corresponding to a yield of 95% of theory) of a yellow to brownish-yellow liquid. This liquid is further purified by distillation in a thin-film evapoarator at 285° C./1–3 mbar. The yellow liquid product has an $n_D20$ of 1.5362.

EXAMPLES 13–17

Using the general procedure of Example 12, alkylation of 2-(2-hydroxy-3,5-di-tert-butylphenyl)-2H-benzotriazole with other 1-alkenes affords the following liquid products.

| Example | 1-Alkene | Yield % of theory | $n_D^{20}$ (of product) |
|---|---|---|---|
| 13 | n-octene | 84 | — |
| 14 | n-decene | 90 | 1.5778 |
| 15 | n-dodecene | 82.9 | 1.5662 |
| 16 | n-tetradecene | 95 | 1.5550 |
| 17 | n-octadecene | 94 | 1.5229 |

EXAMPLE 18

Following the general procedure of Example 12, 286.3 grams of (0.8 mol) of 5-chloro-2-(2-hydroxy-3,5-di-tert-butylphenyl)-2H-benzotriazole are reacted with 165 grams (0.84 mol) of n-tetradecene in the presence of 96.1 grams (1 mol) of methanesulfonic acid to give a liquid product in a yield of 86% of theory.

EXAMPLE 19

Following the procedure of Example 12, 5-chloro-2-(2-hydroxy-3,5-di-tert-butylphenyl)-2H-benzotriazole is reacted with n-octadecene to give a liquid product with an $n_D20$ of 1.5378.

EXAMPLE 20

Following the general procedure of Example 12, 323 grams (1 mol) of 2-(2-hydroxy-5-tert-octylphenyl)-2H-benzotriazole are alkylated with 171.5 grams (1.02 mol) of n-dodecene in the presence of 96.1 grams (1 mol) of methanesulfonic acid to give a liquid product in a 92% yield of theory with an $n_D20$ of 1.5678.

EXAMPLES 21–25

In like manner as is Example 20, 2-(2-hydroxy-5-tert-octylphenyl)-2H-benzotriazole is alkylated with other 1-alkenes to give the following products.

| Example | 1-Alkene | Yield (of theory) | $n_D^{20}$ (of product) |
|---|---|---|---|
| 21 | n-octene | 88 | 1.5757 |
| 22 | n-decene | 100 | 1.5663 |
| 23 | n-tetradecene | 90 | 1.5465 |
| 24 | n-hexadecene | 91 | 1.5436 |
| 25 | n-octadecene | 91.3 | 1.5360 |

EXAMPLE 26

Following the general procedure of Example 12, 351 grams (1 mol) of 2-(2-hydroxy-3,5-di-tert-amylphenyl)-H-benzotriazole are reacted with 200.3 grams (1.02 mol) of n-tetradecene in the presence of 96.1 grams (1 mol) of methanesulfonic acid to give a liquid product in a yield of 88% of theory with an of 1.5293.

EXAMPLES 27–30

In the same manner as in Example 26, 2-(2-hydroxy-3,5-di-tert-amylphenyl)-2H-benzotriazole is alkylated with other 1-alkenes to give the following liquid products.

| Example | 1-Alkene | Yield (% of theory) | $n_D^{20}$ (of product) |
| --- | --- | --- | --- |
| 27 | n-octene | 86 | — |
| 28 | n-decene | 87.5 | 1.5913 |
| 29 | n-dodecene | 82 | 1.5418 |
| 30 | n-octadecene | 87 | 1.5158 |

EXAMPLE 31

Following the procedure of Example 12, 315.8 grams (1 mol) of 5-chloro-2-(2-hydroxy-3-tert-butyl-5-methylphenyl)-2H-benzotriazole are alkylated with 176.5 grams (1.05 mol) of n-dodecene in the presence of 96.1 grams (1 mol) of methanesulfonic acid to give a liquid product in a yield of 57% of theory with an $n_D 20$ of 1.5852.

EXAMPLE 32

A thermoset acrylic resin coating composition, typical for automotive topcoats, is formulated with 2% by weight of the light stabilizer prepared in Example 2. The coating composition is applied to a metal panel and baked at 130° C. to cure the resin. The coated panel is then exposed to accelerated (quick) weathering test (QUV) involving alternating 8-hour period of UV irradiation at 70° C. with a 4-hour period of condensation (rain) at 50° C. for each cycle.

The 20° gloss (ASTM D523 and D2457) and the Distinctness of Image (ASTM E 430) values for the coating before and after weathering in the QUV test are measured and the % retention of 20° gloss and of distinctness of image (D/I) are calculated. The control is the same thermoset acrylic resin coating containing no stabilizer.

The coating containing the instant stabilizer of Example 2 has far better gloss retention, a much higher % retention of D/I and a surface that did not crack compared to the control coating.

The stabilized coating exhibits far superior gloss and D/I retention than the unstabilized control. The stabilized sample shows no sign of surface cracking or crazing again showing the efficacy of the instant compounds as light stabilizers.

EXAMPLE 33

An oil-modified urethane varnish containing 2% by weight of the stabilizer prepared in Example 7 is coated on an aluminum panel and exposed outdoors at a 90° angle facing south in Southern New York for a period of 10.5 months.

The yellowness index (YI), measured by ASTM D 1925, for the sample is measured before exposure and after exposure. The change in YI is a measure of how much the urethane coating discolored over the test period. The lower the change in YI the less discolored is the sample.

The urethane varnish containing the instant benzotriazoles of Example 7 does not yellow whereas the control (without stabilizer) turns perceptively discolored (yellowed).

EXAMPLE 34

Haze Development in Photographic Compositions

The direct assessment of the compatibility of benzotriazole light stabilizers in photographic composition is difficult. The compositions containing such stabilizers in photographic oils often take extended periods of time for separation or haze to be observed.

An important property of photographic compositions directly related to such compatibility parameters is haze. For the preparation of clear and precise photographic images, haze must obviously be minimized or better yet essentially eliminated.

Using the procedure described in U.S. Pat. No. 4,383,863, Example 5, a UV-protecting layer is prepared in gelatin containing an anionic wetting agent, a hardener and the instant stabilizer of Example 10 using no solvent.

A very fine dispersion of the instant stabilizer in this gelatin composition is produced by ultrasonic mixing to give a UV-protecting layer which is clear and transparent and exhibits no haze.

What is claimed is:

1. A stabilized composition which comprises
   (a) an organic polymer subject to light-induced deterioration, and
   (b) an effective stabilizing amount of a normally liquid or non-crystalline mixture of benzotriazoles, suitable for stabilizing an organic polymer against light-induced deterioration, which consists essentially of compounds of formula I

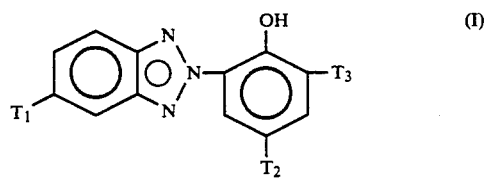

wherein
   $T_1$ is hydrogen, chloro, alkyl of 1 to 4 carbon atoms or alkoxy of 1 to 4 carbon atoms, and in major proportions compounds
   where one of $T_2$ or $T_3$ is a random statistical mixture of at least three isomeric alkyl groups each having 8 to 40 carbon atoms; and
   the other of $T_2$ or $T_3$ is hydrogen or methyl, and
   where one of $T_2$ or $T_3$ is a random statistical mixture as defined above and the other of $T_2$ or $T_3$ is alkyl of 2 to 12 carbon atoms, cycloalkyl of 5 to 8 carbon atoms or aralkyl of 7 to 9 carbon atoms; and
   in minor proportions compounds where both of $T_2$ and $T_3$ are a random statistical mixture as defined above or where the compounds represent dealkylated or fragmented-alkyl substituted products of the benzotriazoles of formula I
   which mixture is prepared by reacting a 2H-benzotriazole of formula (A) or (B)

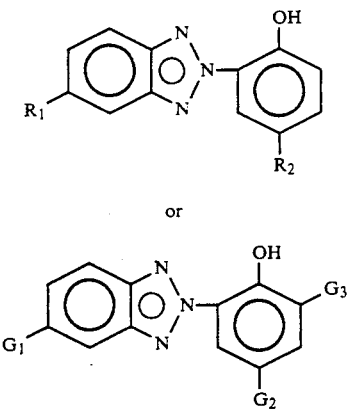

where
R₁ is hydrogen, chloro, alkyl of 1 to 4 carbon atoms or alkoxy of 1 to 4 carbon atoms,
R₂ is alkyl of 2 to 12 carbon atoms, cycloalkyl or 5 to 8 carbon atoms or aralkyl of 7 to 9 carbon atoms,
G₁ has the same meaning as R₁, and
G₂ and G₃ are independently branched alkyl of 3 to 12 carbon atoms, cycloaklyl of 5 to 8 carbon atoms or aralkyl of 7 to 9 carbon atoms, or one of G₂ and G₃ is methyl or ethyl when the other of G₂ and G₃ is branched alkyl, cycloalkyl or aralkyl as defined above,
with a straight or branched chain alkene of 8 to 40 carbon atoms or mixture of said alkenes in the presence of an acidic catalyst at a temperature of 100° to 200° C.

2. A stabilized composition according to claim 1, wherein the organic polymer is a polyolefin, a styrene polymer, a polyacrylate, a polyamide, a polyurethane, a halogen containing vinyl polymer, an alkyd resin, a thermoset acrylic resin or an epoxy resin.

3. A composition according to claim 1 wherein the compounds of formula I, T₁ is hydrogen or chloro.

4. A composition according to claim 3 wherein T₁ is hydrogen.

5. A composition according to claim 1 where in the compounds of formula I, T₂ or T₃ in the random statistical mixture of alkyl groups is alkyl of 8 to 16 carbon atoms.

6. A composition according to claim 5 wherein T₂ or T₃ is alkyl of 10 to 12 carbon atoms.

7. A composition according to claim 1 where in the compounds of formula I, T₂ or T₃ is hydrogen, branched alkyl of 4 to 8 carbon atoms or α,α-dimethylbenzyl, but T₂ and T₃ are not both hydrogen at the same time.

* * * * *

UNITED STATES PATENT AND TRADEMARK OFFICE
CERTIFICATE OF CORRECTION

PATENT NO. : 5,095,062

DATED : MARCH 10, 1992

INVENTOR(S) : ROLAND A.E. WINTER, ET AL.

It is certified that error appears in the above-identified patent and that said Letters Patent is hereby corrected as shown below:

On the cover page, Item [75], second line, should read
-- Robert E. Detlefsen, Putnam Valley, --.

Signed and Sealed this

Fourth Day of January, 1994

*Attest:*

BRUCE LEHMAN

*Attesting Officer*  *Commissioner of Patents and Trademarks*